(12) United States Patent
Waters et al.

(10) Patent No.: US 8,201,842 B1
(45) Date of Patent: Jun. 19, 2012

(54) LIMB ELEVATING ACCESSORY

(76) Inventors: David Waters, Bakersfield, CA (US);
Barbara Waters, legal representative,
Bakersfield, CA (US); Brian Neal,
Bakersfield, CA (US); Gary Neal,
Bakersfield, CA (US); Cecil Neal,
Bakersfield, CA (US)

( * ) Notice: Subject to any disclaimer, the term of this patent is extended or adjusted under 35 U.S.C. 154(b) by 0 days.

(21) Appl. No.: 12/906,609

(22) Filed: Oct. 18, 2010

(51) Int. Cl.
*A61G 5/10* (2006.01)
(52) U.S. Cl. .................... 280/304.1; 280/250.1
(58) Field of Classification Search .......... 280/304.1, 280/250.1, 291; 5/624, 649, 621, 622, 623, 5/651, 646, 647; 297/423.17–423.19, 423.25
See application file for complete search history.

(56) References Cited

U.S. PATENT DOCUMENTS

| | | | | |
|---|---|---|---|---|
| 3,222,029 A * | 12/1965 | Hildemann | ............ | 254/8 R |
| 3,765,411 A * | 10/1973 | Ward, Jr. | ............ | 602/35 |
| 4,407,496 A * | 10/1983 | Johnson | ............ | 482/97 |
| 4,572,577 A * | 2/1986 | LaRue | ............ | 297/423.2 |
| 4,809,687 A * | 3/1989 | Allen | ............ | 602/4 |
| 5,378,041 A * | 1/1995 | Lee | ............ | 297/391 |
| D367,118 S * | 2/1996 | Miller et al. | ............ | D24/188 |
| D399,966 S * | 10/1998 | Brown et al. | ............ | D24/190 |
| 5,906,415 A * | 5/1999 | Mocur | ............ | 297/423.3 |
| 6,155,586 A * | 12/2000 | Melgarejo et al. | ............ | 280/304.1 |
| 6,704,959 B2 * | 3/2004 | Schuerch | ............ | 5/648 |
| 6,709,369 B1 * | 3/2004 | Jacobs | ............ | 482/80 |
| 6,874,184 B2 * | 4/2005 | Chandler | ............ | 5/648 |
| 7,303,513 B1 * | 12/2007 | Curtiss | ............ | 482/130 |
| 2002/0193210 A1 * | 12/2002 | Turner | ............ | 482/80 |
| 2003/0182726 A1 * | 10/2003 | Greenfield et al. | ............ | 5/648 |
| 2006/0071531 A1 * | 4/2006 | Groth | ............ | 297/423.26 |
| 2007/0001502 A1 * | 1/2007 | Welsh et al. | ............ | 297/423.4 |
| 2007/0089239 A1 * | 4/2007 | Whiteside | ............ | 5/624 |
| 2008/0172791 A1 * | 7/2008 | Walczyk | ............ | 5/623 |
| 2010/0237215 A1 * | 9/2010 | Dahl | ............ | 248/419 |

* cited by examiner

*Primary Examiner* — Tashiana Adams
(74) *Attorney, Agent, or Firm* — Kyle Fletcher (57) ABSTRACT

The limb elevating accessory can attach itself onto an existing wheelchair and provide a means to support and elevate a limb of an end user seated therein. The limb elevating accessory includes a base support that attaches onto the frame of the wheelchair, and also attaches to an upper support. The upper support has a plurality of holes from which a stirrup or support attaches to support an arm or a leg thereon. The base support also includes an adjustable hook that hooks at a second location to the frame of the wheelchair in order to further stabilize the accessory upon the wheelchair.

13 Claims, 6 Drawing Sheets

LIMB ELEVATING ACCESSORY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of wheelchairs, more specifically, a wheelchair accessory that can elevate limbs.

Infections can attack any part of the body, and can cause severe problems if left untreated. It is a well-known fact that if there is an infection in a limb, the key to overcoming said infection is to elevate the respective limb. This is especially poignant when the individual is limited in mobility to a wheelchair.

The present invention seeks to improve upon this dilemma by providing an end user with an accessory that attaches onto a wheelchair and of which is specifically suited for elevating a limb so as to combat an infection or edema associated with the respective limb. Even more particularly, the present invention enables the end user to be mobile while healing is obtained, and therefore the morale of the end user is heightened.

B. Discussion of the Prior Art

As a preliminary note, it should be stated that there is an ample amount of prior art that deals with wheelchair accessories. As will be discussed immediately below, no prior art discloses a wheelchair accessory that can attach upon a wheelchair and of which provides a means for elevating a limb; wherein the accessory does not require any outfitting of the wheelchair; wherein the accessory includes a bracket that clamps onto an existing portion of the wheelchair along with an adjustable hook that provides for greater overall stability of the accessory; wherein the accessory has adjustable supports that enable support of an arm or a leg of different sized end users.

The Ward, Jr. Patent (U.S. Pat. No. 3,765,411) discloses a portable traction apparatus that provides a patient with mobility in bed, as well as freedom to use a wheelchair while maintaining substantially constant tractive force on the fractured member. However, the apparatus does not attach onto a wheelchair and provide a means of supporting a limb thereon in order to elevate said limb for combating infections.

The Groth Patent Application Publication (U.S. Pub. No. 2006/0071531) discloses a leg amputee support assembly that includes a seat, a limb support, and a pivot point disposed between the seat and limb support for use with a wheelchair. However, the support assembly is directed to the support of a leg amputee and not the support of a limb at an elevated position irregardless of whether the limb is amputated.

The LaRue Patent (U.S. Pat. No. 4,572,577) discloses a portable seat for disposition in a chair comprising a seat section on which a leg amputee sits and slidable leg-supporting sections on which a residual limb is supported. Again, the support assembly is directed to the support of a leg amputee and not the support of a limb at an elevated position irregardless of whether the limb is amputated.

The Mocur Patent (U.S. Pat. No. 5,906,415) discloses a wheelchair provided with special seats having hinged connections with leg supports locable in proximity to the seat front edge to provide resting surfaces for amputated legs of disabled persons. Again, the special seat is designed to support amputated legs thereon and not to elevate a leg or arm irregardless of amputation.

The Allen Patent (U.S. Pat. No. 4,809,687) discloses a medical stirrup for supporting a patient's limb that is retained in a shell lined with a soft material suspended from an adjustable support by straps. However, the medical stirrup does not attach itself onto either side of a wheelchair and provide an accessory to said wheelchair that can support a limb of an end user at an elevated position while simultaneously seated in said wheelchair.

The Miller et al. Patent (U.S. Pat. No. Des. 367,118) illustrates a design for a traction unit, which does not depict an accessory for a wheelchair that supports a limb at an elevated position.

While the above-described devices fulfill their respective and particular objects and requirements, they do not describe a wheelchair accessory that can attach upon a wheelchair and of which provides a means for elevating a limb; wherein the accessory does not require any outfitting of the wheelchair; wherein the accessory includes a bracket that clamps onto an existing portion of the wheelchair along with an adjustable hook that provides for greater overall stability of the accessory; wherein the accessory has adjustable supports that enable support of an arm or a leg of different sized end users. In this regard, the limb elevating accessory departs from the conventional concepts and designs of the prior art.

SUMMARY OF THE INVENTION

The limb elevating accessory can attach itself onto an existing wheelchair and provide a means to support and elevate a limb of an end user seated therein. The limb elevating accessory includes a base support that attaches onto the frame of the wheelchair, and also attaches to an upper support. The upper support has a plurality of holes from which a stirrup or support attaches to support an arm or a leg thereon. The base support also includes an adjustable hook that hooks at a second location to the frame of the wheelchair in order to further stabilize the accessory upon the wheelchair.

A further object of the invention is to provide a wheelchair accessory that can attach onto an existing wheelchair and of which can support a limb at an elevated position while an end user is seated in said wheelchair.

A further object of the invention is to provide a wheelchair accessory that clamps and hooks onto various points of a wheelchair frame, and may or may not require any permanent installation thereon.

A further object of the invention is to provide an accessory that elevates an arm or leg of an end user seated in a wheelchair in order to combat infections in the respective limb while providing mobility to the end user.

A further object of the invention is to provide an upper support that has a plurality of holes upon which the stirrup or support can attach in order to provide adjustable elevations for use of the accessory for varying needs.

These together with additional objects, features and advantages of the limb elevating accessory will be readily apparent to those of ordinary skill in the art upon reading the following detailed description of presently preferred, but nonetheless illustrative, embodiments of the limb elevating accessory when taken in conjunction with the accompanying drawings.

In this respect, before explaining the current embodiments of the limb elevating accessory in detail, it is to be understood that the limb elevating accessory is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the limb elevating accessory.

It is therefore important that the claims be regarded as including such equivalent construction insofar as they do not depart from the spirit and scope of the limb elevating accessory. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-7. A limb elevating accessory 100 (hereinafter invention) includes a base support 101 and an upper support 102.

The base support 101 attaches onto a wheelchair 103 via a plurality of means including welding or a clamp 104. The clamp 104 includes a base plate 105 having a first semi-circular groove 106 and a second semi-circular groove 107 thereon. A first top plate 108 attaches adjacent the first semi-circular groove 106 via a hinge 109; and a second top plate 110 attaches adjacent the second semi-circular groove 107 via a hinge 111. The first top plate 108 and the second top plate 110 can each rotate over the respect portion of the base plate 105 to form a hollowed opening 112. A bottom plate 113 having a plurality of holes 114 can bolt to holes 115 located on the base plate 105, first top plate 108, and the second top plate 110 via bolt 116 and nut 117. The two hollowed openings 112 are designed to accommodate both the base support 101 and a lower frame 118 of the wheelchair (see FIG. 1).

The base support 101 includes a bend 119 upon which a portion of the base support 101 extends Vertically. Near a top end of the base support 101 is a hole 120 upon which an adjustable hook 121 attaches. The adjustable hook 121 includes a hook 122 with a threaded end that is inserted through the hole 120 of the base support 101 and is secured thereon via a threaded cap 123. The adjustable hook 121 further includes an adjustable eyelet 124 that attaches at a first end 125 to the hook 122. A second end 126 of the adjustable eyelet 124 hooks onto an upper frame 127 of the wheelchair 103 (see FIG. 1). The inclusion of the adjustable hook 121 is to provide greater stability to the invention 100 with respect to the wheelchair 103.

It shall be noted that the invention is self-supporting, and does not require an additional means of supporting the invention 100 with respect to the ground. In other words, there is no requirement for an additional caster wheel to support the invention 100 outside of the wheelchair 103.

Figure 1:
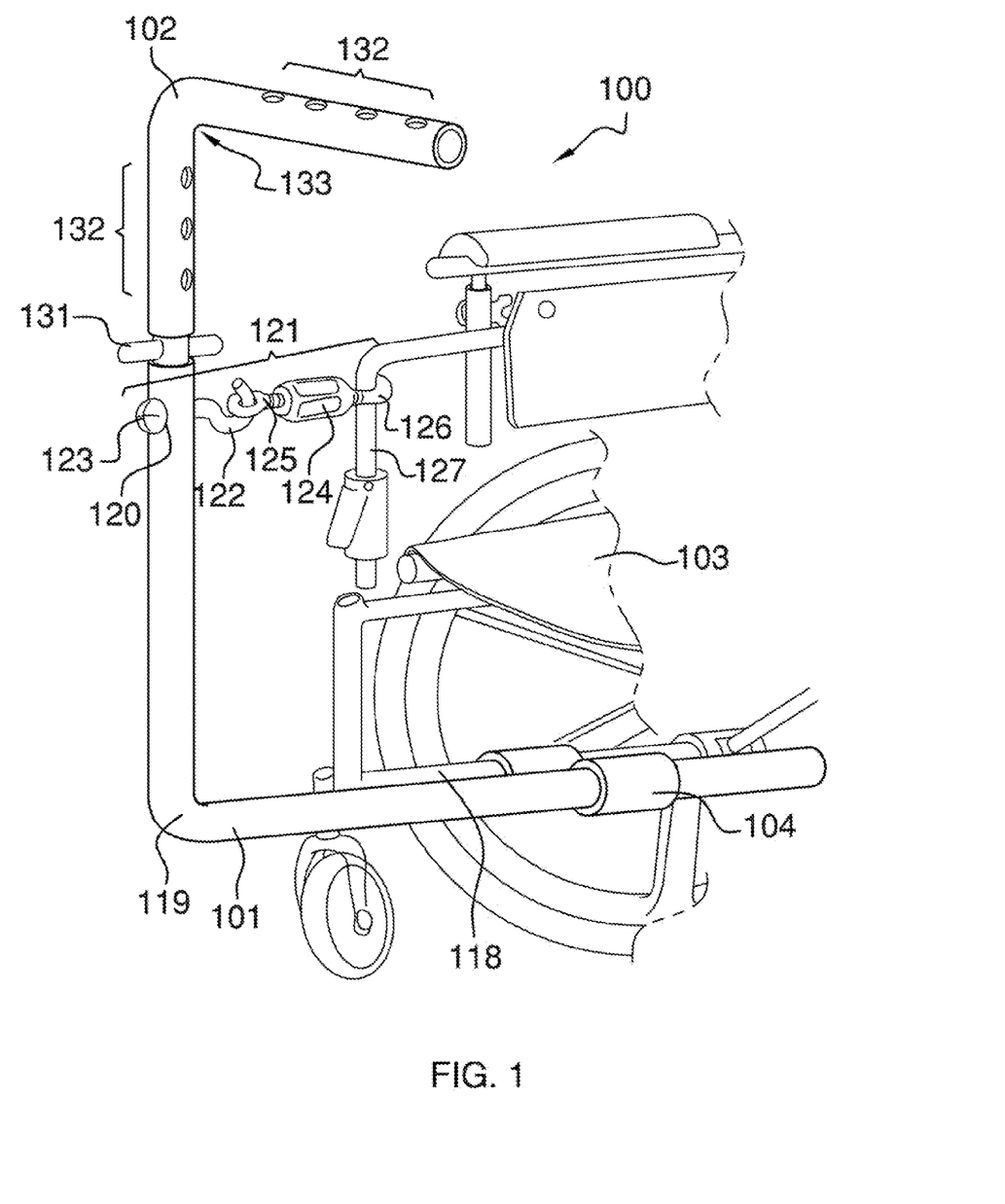
FIG. 1 illustrates a front, isometric view of the limb elevating accessory installed upon an existing wheelchair, and detailing the bracket clamped onto the wheelchair as well as detailing the adjustable hook that attaches at a different point on the wheelchair.
Figure 2:
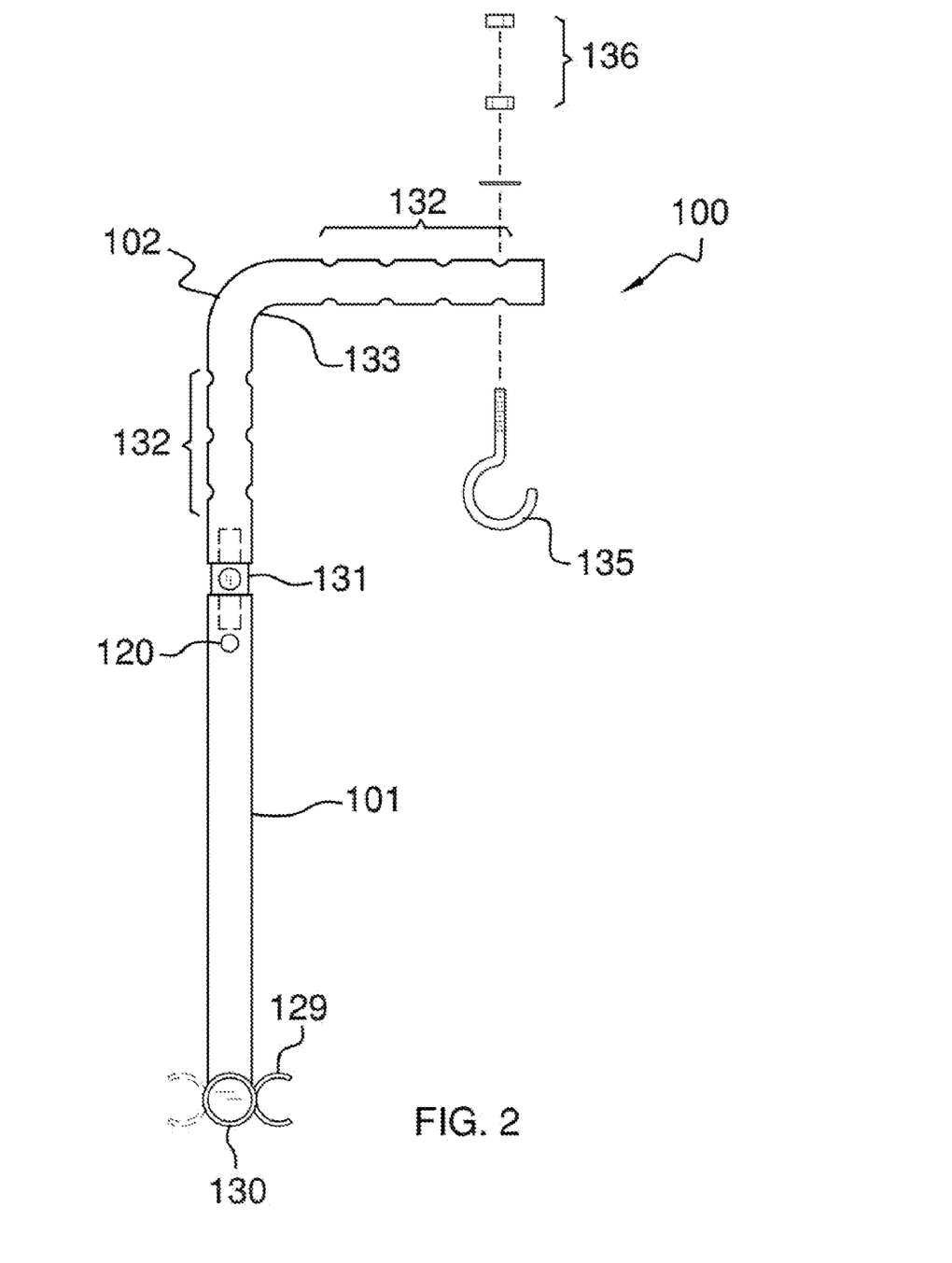
FIG. 2 illustrates a front view of the limb elevating accessory by itself and wherein the hook for supporting the limb is exploded, and the bracket is depicted in a left or right orientation, and wherein the 4-way insert is partially depicted in dashed lines to indicate the location within both the base support and the upper support.
Figure 3:
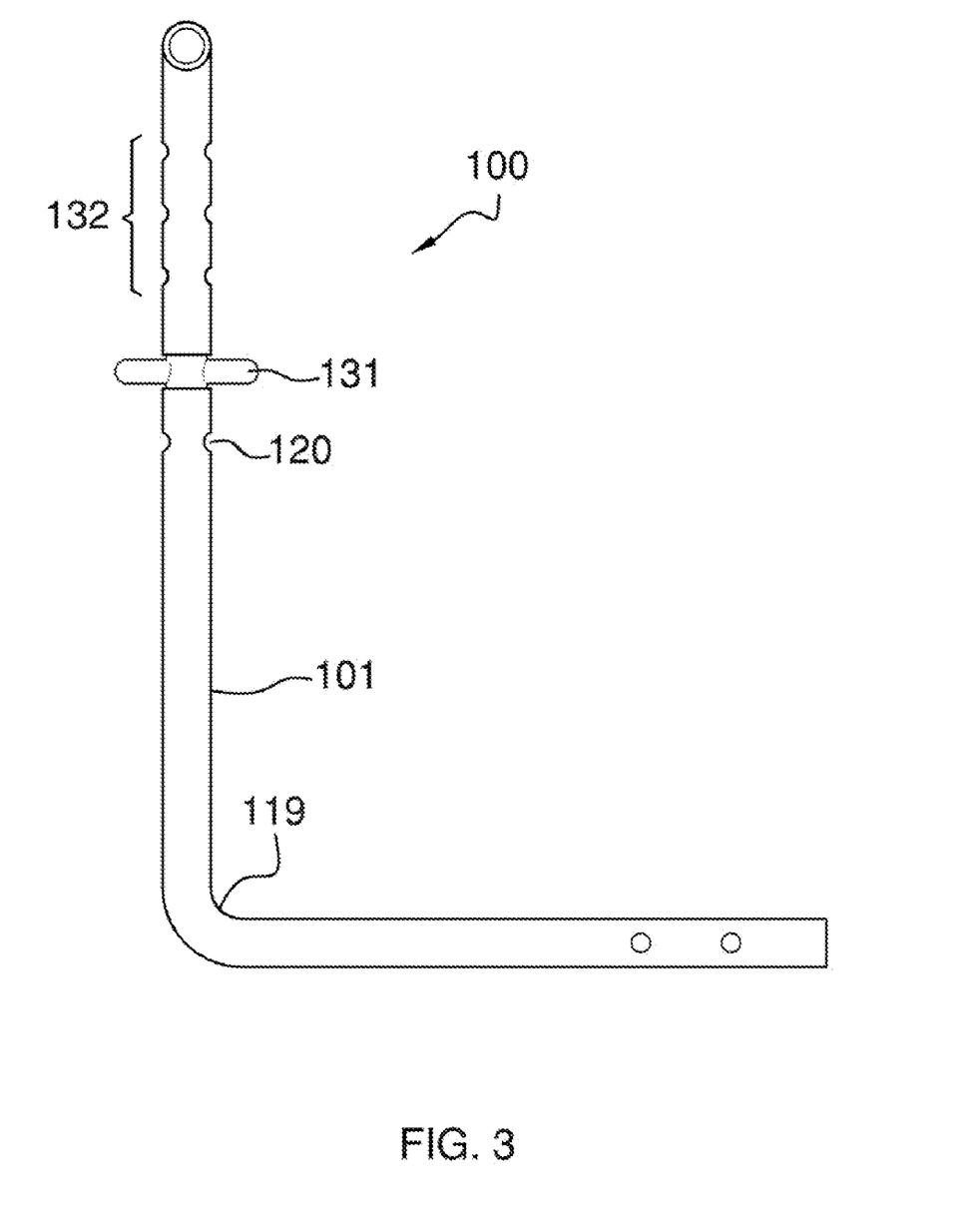
FIG. 3 illustrates a side view of the limb elevating accessory in an assembled state and by itself, and detailing the various attachment holes on the base support.
Figure 4:
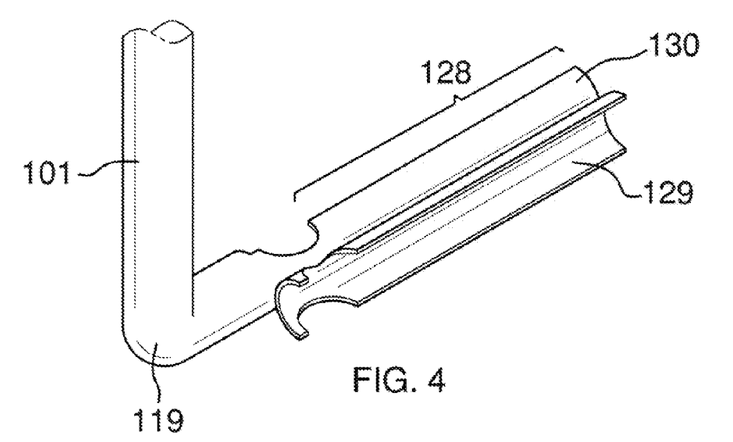
FIG. 4 illustrates an isometric view of the connection detail wherein the base support is depicted with a connection oriented on a left side.
Figure 5:
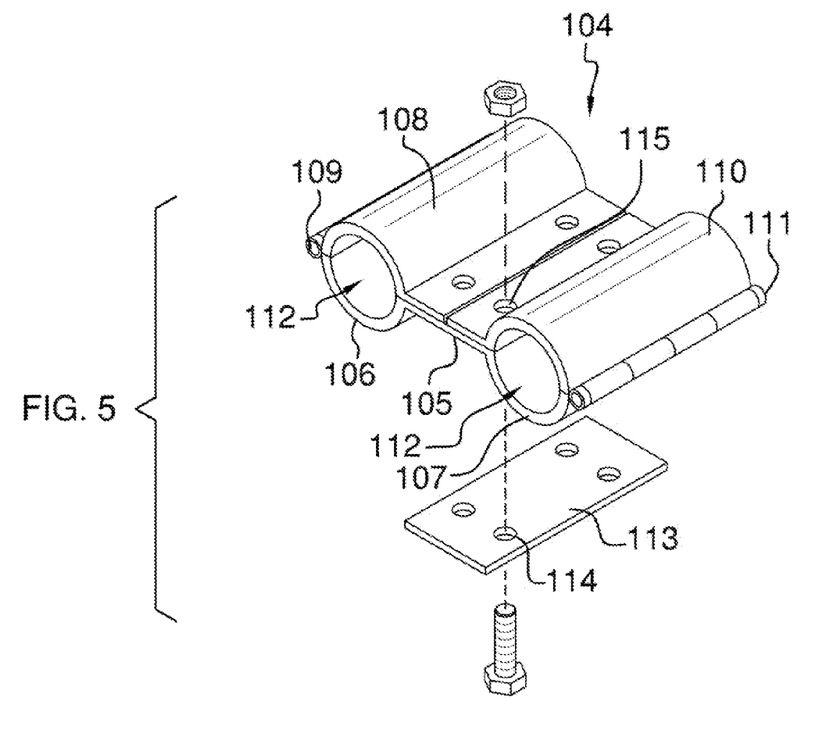
FIG. 5 illustrates an isometric view of the connection detail of an alternative embodiment that can be oriented on a left or right of a wheelchair.
Figure 6:
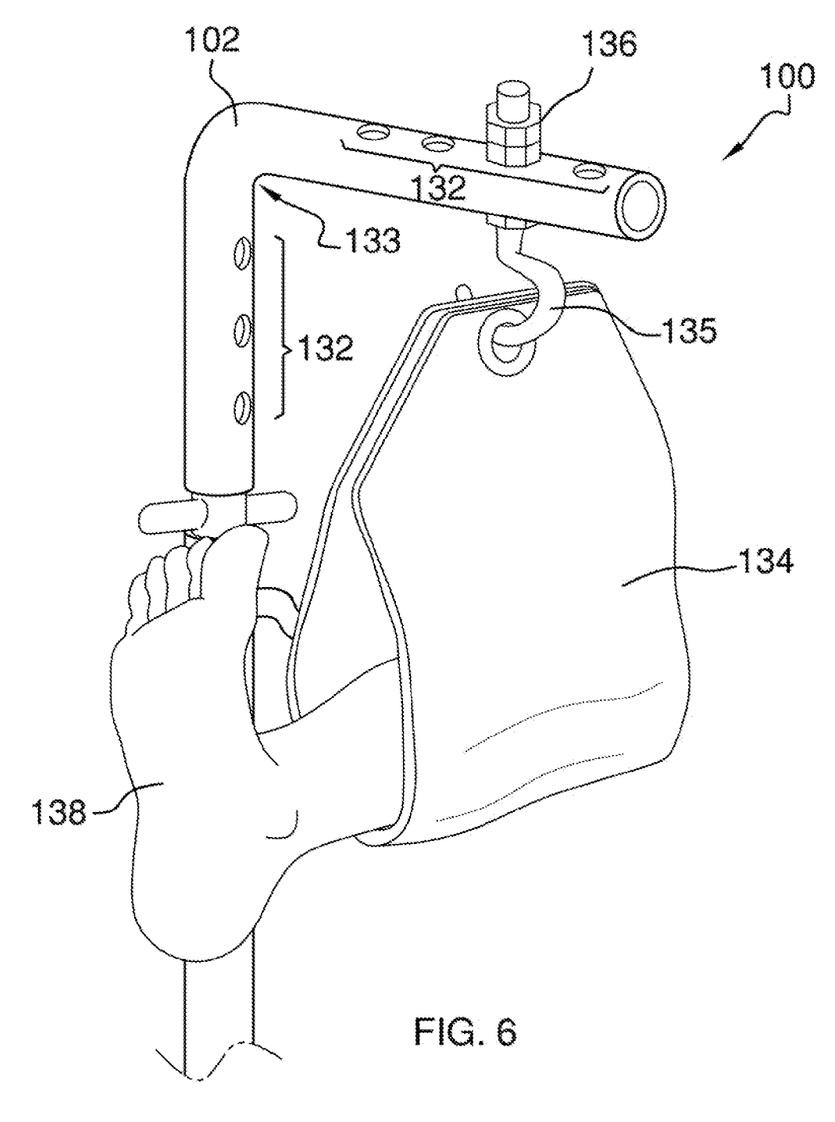
FIG. 6 illustrates an isometric view of the limb elevating accessory in use and supporting a limb via the hook and support.

Referring to FIGS. 2 and 4, the clamp 104 may be replaced by a mount bracket 128 that is integrated into the design of the base support 101. The shape of the mount bracket 128 is such that the mount bracket 128 can attach on a left or right side of the wheelchair 103 at the lower frame 118. The mount bracket 128 has a right protruding member 129 that is semi-circularly shaped and tangentially attached along the length of the mount bracket 128. The right protruding member 129 is designed to enable attachment of the mount bracket 128 on right side of the wheelchair 103. A left member 130 mirrors the right protruding member 129, and enables attachment of the mount bracket 128 to the left side of the wheelchair 103.

Figure 7:
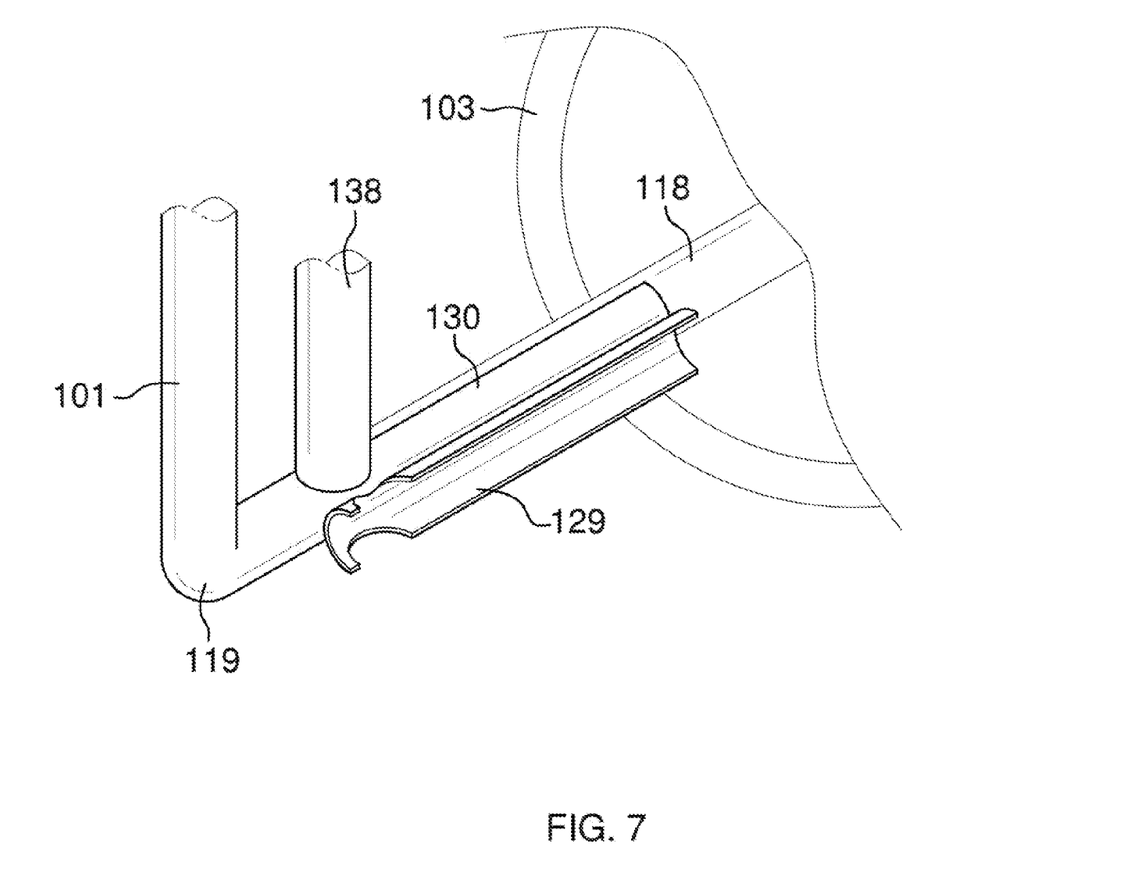
FIG. 7 illustrates an isometric view of the mount bracket attached to the wheelchair to illustrate the inter-play of the various pieces of the frame of the wheelchair with respect to the mount bracket.

Both the left protruding member 130 and the right protruding member 129 have semi-circular cutouts 131 to accommodate attachment of the mount bracket 128 to the wheelchair 103 and to a vertical frame member 131 of the wheelchair (see FIG. 7). It shall be noted that the use of the mount bracket 128 requires welding in order to secure the mount bracket 128 to the wheelchair 103.

It shall be hereby noted that the clamp 104 and the mount bracket 128 may be referred to as attaching means.

The base support 101 connects to the upper support 102 via a 4-way support 131. The 4-way support 131 enables the upper support 102 to be secured atop the base support 101, but also enables the upper support 102 to rotate thereon.

The upper support 102 includes a plurality of holes 132 along a bottom portion of the upper support 102 as well as along a top portion of the upper support 102. The upper support 102 includes a 90 degree bend 133.

A stirrup 134 attaches to the upper support 102 via a hook 135. The hook 135 has a threaded end that passes into one of the holes 132 of the upper support 102 and is secured thereon via at least one nut 136. It shall be noted that a washer 137 may be included and used to further secure the hook 135 to the upper support 102.

The stirrup 134 is used to support a limb 138 thereon. The elevation of the stirrup 134 with respect to the wheelchair 103 may be adjusted by relocating the hook 135 at one of the various holes 132 located throughout the upper support 102, which will offer greater flexibility in use as to accommodate end users of different statures as well as providing a means to support all limbs (either legs or arms).

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

We claim:

1. A limb elevating accessory comprising:
    a base support that attaches onto a frame of a wheelchair via attaching means comprising a clamp;
    wherein an upper support attaches atop said base support and includes a plurality of holes upon which a hook can be bolted thereon, and wherein a stirrup attaches to said hook in order to provide a means of elevating a limb of an end user seated in said wheelchair, and wherein the accessory is self-supporting;
    wherein the clamp includes a base plate having a first semi-circular groove and a second semi-circular groove thereon; wherein a first top plate attaches adjacent the first semi-circular groove via a hinge; and a second top plate attaches adjacent the second semi-circular groove via a hinge; wherein the first top plate and the second top plate can each rotate over the respect portion of the base plate to form a hollowed opening; wherein a bottom plate having a plurality of holes can bolt to holes located on the base plate, first top plate, and the second top plate via bolt and nut; wherein the two hollowed openings are designed to accommodate both the base support and a lower frame of the wheelchair;
    wherein the base support includes a bend upon which a portion of the base support extends vertically;
    wherein the base support has a hole upon which an adjustable hook attaches onto an upper frame of the wheelchair.

2. The limb elevating accessory as described in claim 1 wherein the adjustable hook includes a hook with a threaded end that is inserted through the hole of the base support and is secured thereon via a threaded cap.

3. The limb elevating accessory as described in claim 2 wherein the adjustable hook further includes an adjustable eyelet that attaches at a first end to the hook; wherein a second end of the adjustable eyelet hooks onto an upper frame of the wheelchair.

4. The limb elevating accessory as described in claim 1 wherein the base support connects to the upper support via a 4-way support; wherein the 4-way support enables the upper support to be secured atop the base support, but also enables the upper support to rotate thereon.

5. The limb elevating accessory as described in claim 1 wherein the stirrup attaches to the upper support via a hook; wherein the hook has a threaded end that passes into one of the holes of the upper support and is secured thereon via at least one nut.

6. A limb elevating accessory comprising:
    a base support that attaches onto a frame of a wheelchair via a clamp;
    wherein the clamp includes a base plate having a first semi-circular groove and a second semi-circular groove thereon; wherein a first top plate attaches adjacent the first semi-circular groove via a hinge; and a second top plate attaches adjacent the second semi-circular groove via a hinge; wherein the first top plate and the second top plate can each rotate over the respect portion of the base plate to form a hollowed opening; wherein a bottom plate having a plurality of holes can bolt to holes located on the base plate, first top plate, and the second top plate via bolt and nut; wherein the two hollowed openings are designed to accommodate both the base support and a lower frame of the wheelchair;
    wherein an upper support attaches atop said base support and includes a plurality of holes upon which a hook can be bolted thereon, and wherein a stirrup attaches to said hook in order to provide a means of elevating a limb of an end user seated in said wheelchair, and wherein the accessory is self-supporting;
    wherein the stirrup attaches to the upper support via a hook; wherein the hook has a threaded end that passes into one of the holes of the upper support and is secured thereon via at least one nut.

7. The limb elevating accessory as described in claim 6 wherein the base support includes a bend upon which a portion of the base support extends vertically.

8. The limb elevating accessory as described in claim 6 wherein the base support has a hole upon which an adjustable hook attaches onto an upper frame of the wheelchair; wherein the adjustable hook includes a hook with a threaded end that is inserted through the hole of the base support and is secured thereon via a threaded cap; wherein the adjustable hook further includes an adjustable eyelet that attaches at a first end to the hook; wherein a second end of the adjustable eyelet hooks onto an upper frame of the wheelchair.

9. The limb elevating accessory as described in claim 6 wherein the base support connects to the upper support via a 4-way support; wherein the 4-way support enables the upper support to be secured atop the base support, but also enables the upper support to rotate thereon.

10. A limb elevating accessory comprising:
    a base support that attaches onto a frame of a wheelchair via a mount bracket;
    wherein the mount bracket is integrated into the design of the base support and has a right protruding member that is semi-circularly shaped and tangentially attached along the length of the mount bracket, and enables attachment of the mount bracket to a right side of the wheelchair; wherein a left protruding member mirrors the right protruding member, and enables attachment of the mount bracket to the left side of the wheelchair;

wherein the left protruding member and the right protruding member have semi-circular cutouts to accommodate attachment of the mount bracket to a vertical frame member of the wheelchair; and wherein the mount bracket requires welding in order to secure the mount bracket to the wheelchair, and wherein the accessory is self-supporting;

wherein an upper support attaches atop said base support and includes a plurality of holes upon which a hook can be bolted thereon, and wherein a stirrup attaches to said hook in order to provide a means of elevating a limb of an end user seated in said wheelchair;

wherein the base support has a hole upon which an adjustable hook attaches onto an upper frame of the wheelchair; wherein the adjustable hook includes a hook with a threaded end that is inserted through the hole of the base support and is secured thereon via a threaded cap; wherein the adjustable hook further includes an adjustable eyelet that attaches at a first end to the hook; wherein a second end of the adjustable eyelet hooks onto an upper frame of the wheelchair.

11. The limb elevating accessory as described in claim 10 wherein the base support includes a bend upon which a portion of the base support extends vertically.

12. The limb elevating accessory as described in claim 10 wherein the base support connects to the upper support via a 4-way support; wherein the 4-way support enables the upper support to be secured atop the base support, but also enables the upper support to rotate thereon.

13. The limb elevating accessory as described in claim 10 wherein the stirrup attaches to the upper support via a hook; wherein the hook has a threaded end that passes into one of the holes of the upper support and is secured thereon via at least one nut.

* * * * *